US006709854B2

(12) United States Patent
Donahue, Jr. et al.

(10) Patent No.: US 6,709,854 B2
(45) Date of Patent: Mar. 23, 2004

(54) METHOD CAPABLE OF INCREASING COMPETENCY OF BACTERIAL CELL TRANSFORMATION

(75) Inventors: Robert A. Donahue, Jr., Falls Church, VA (US); Robert L. Bebee, Gaithersburg, MD (US)

(73) Assignee: Invitrogen Corporation, Carlsbad, CA (US)

( * ) Notice: Subject to any disclaimer, the term of this patent is extended or adjusted under 35 U.S.C. 154(b) by 208 days.

(21) Appl. No.: 09/895,202

(22) Filed: Jul. 2, 2001

(65) Prior Publication Data

US 2001/0046698 A1 Nov. 29, 2001

Related U.S. Application Data

(63) Continuation of application No. 08/790,820, filed on Jan. 30, 1997, now Pat. No. 6,274,369.
(60) Provisional application No. 60/011,040, filed on Feb. 2, 1996.

(51) Int. Cl.$^7$ .................................................. C12N 1/20
(52) U.S. Cl. ................................ 435/252.33; 435/252.8
(58) Field of Search ........................ 435/252.8, 252.33, 435/440, 476, 488

(56) References Cited

U.S. PATENT DOCUMENTS

| | | | |
|---|---|---|---|
| 3,843,453 A | 10/1974 | Freake et al. ............. | 195/103.5 |
| 4,038,143 A | 7/1977 | Juni ........................... | 195/100 |
| 4,446,230 A | 5/1984 | Zubrzycki ...................... | 435/6 |
| 4,520,019 A | 5/1985 | Ribi et al. ................ | 424/195.1 |
| 4,681,852 A | 7/1987 | Tribe .......................... | 435/108 |
| 4,808,404 A | 2/1989 | Bhogal ......................... | 424/88 |
| 4,824,938 A | 4/1989 | Koyama et al. ............. | 530/351 |
| 4,851,348 A | 7/1989 | Hanahan ................. | 435/252.33 |
| 4,891,319 A | 1/1990 | Roser .......................... | 435/188 |
| 4,950,609 A | 8/1990 | Tischer et al. ................ | 435/18 |
| 4,981,797 A | 1/1991 | Jessee et al. .............. | 435/172.3 |
| 5,045,446 A | 9/1991 | Goodrich, Jr. et al. .......... | 435/2 |
| 5,059,518 A | 10/1991 | Kortright et al. .............. | 435/6 |
| 5,098,893 A | 3/1992 | Franks et al. ................. | 514/54 |
| 5,292,507 A | 3/1994 | Charley ....................... | 424/93 |
| 5,425,951 A | 6/1995 | Goodrich, Jr. et al. ...... | 424/520 |
| 5,512,468 A | 4/1996 | Greener ................... | 435/172.3 |
| 5,891,692 A | 4/1999 | Bloom et al. ............ | 435/172.3 |

FOREIGN PATENT DOCUMENTS

| | | |
|---|---|---|
| AU | A-27434/88 | 6/1989 |
| EP | 0 383 569 A2 | 8/1990 |
| EP | 0 508 496 A1 | 10/1992 |
| WO | WO 98/49266 | 11/1998 |

OTHER PUBLICATIONS

Anderson, D.M.W. and I.C.M. Dea, "Recent advances in the chemistry of Acacia gums," *J. Soc. Cosmet. Chem.* 22:61–76, Society of Cosmetic Chemists of Great Britain (1971).

Alexander, D.C: et al., "A simplified and efficient vector–primer cDNA cloning system," *Gene 31*:79–89, Elsevier Science (1984).

Chung, C.T. et al., "One–step prepartion of competent *Escherichia coli*: Transformation and storage of bacterial cells in the same solution," *Proc. Natl. Acad. Sci. USA 86*:2172–2175, The National Academy of Sciences (1989).

Cosloy, S.D. and M. Oishi, "Genetic Transformation in *Escherichia coli* K12," *Proc. Natl. Acad. Sci. USA 70*:84–87, The National Academy of Sciences (1973).

Cronan, Jr., J.E., "Thermal Regulation of the Membrane Lipid Compostion of *Escherichia coli*," *J. Biol. Chem. 250*:7074–7077, American Society for Biochemistry and Molecular Biology (1975).

Crowe, J.H. et al., "Stabilization of dry phospholipid bilayers and proteins by sugars," *Biochem. J. 242*:1–10, American Chemical Soceity (1987).

Danilevskaya, O.N. and A.I. Gragerov, "Curing of *Escherichia coli* K12 Plasmids by Coumermycin," *Molec. Gen. Genet. 178*:233–235, Springer Verlag (1980).

de Mendoza, D. et al., "Overproduction of cis–Vaccenic Acid and Altered Temperature Control of Fatty Acid Synthesis in a Mutant of *Escherichia coli*," *J. Bacteriol. 151*:1608–1611, American Society for Microbiololgy (1982).

de Mendoza, D. et al., "Thermal Regulation of Membrane Fluidity in *Escherichia coli*," *J. Biol. Chem. 258*:2098–2101, American Society for Biochemistry and Molecular Biology (1983).

de Mendoza, D. and J.E. Cronan, Jr., "Thermal regulation of membrane lipid fluidity in bacteria," *TIBS 8*:49–52, Elsevier Science (1983).

Dityatkin, S. Ya. and B.N. Il'yashenko, "Acceptor properties of freeze–thawed bacteria in relation to isolated plasmid DNA," *Chem. Abs. 89*:295, Abstract No. 176192r, The American Chemical Society (1978).

Dityatkin, S.Ya. and B.N. Ilyashenko, "Frozen and thawed bacteria as recipients of isolated phage and plasmid DNA," *Chem. Abs. 90*:322, Abstract No. 183010d, The American Chemical Society (1979).

Dutyatkin, S. Ya. and B.N. Il'yashenko, "Chromosomal transformation of frozen–thawed bacteria," *Chem. Abs. 90*:286–287, Abstract No. 148301c, The American Chemical Society (1979).

(List continued on next page.)

*Primary Examiner*—Nashaat T. Nashed
(74) *Attorney, Agent, or Firm*—Sterne, Kessler, Goldstein & Fox P.L.L.C.

(57) ABSTRACT

The invention concerns bacterial strains capable of enhanced transformation efficiencies that are produced by the introduction of the F' genetic material. The invention also concerns processes for producing transformable competent bacteria with enhanced transformation efficiencies.

17 Claims, No Drawings

OTHER PUBLICATIONS

Gombos, Z. et al., "Unsaturation of fatty acids in membrane lipids enhances tolerance of the cyanobacterium Synechocystis PCC6803 to low–temperature photoinhibition," *Proc. Natl. Acad. Sci. USA* 89:9959–9963, The National Academy of Sciences (1992).

Green, J.L. and C.A. Angell, "Phase Relations and Vitrification in Saccharide–Water Solutions and the Trehalose Anomaly," *J. Phys. Chem.* 93:2880–2882, American Chemical Society (1989).

Hanahan, D., "Techniques for Transformation of *E. coli*," in *DNA cloning. vol. I. a practical approach*, Glover, D.M., ed., IRL Press Limited, Oxford, England, pp. 109–135 (1985).

Hanahan, D. et al., "Plasmid Transformation of *Escherichia coli* and Other Bacteria," *Meth. Enzym.* 204:63–113, Academic Press, Inc. (1991).

Hatley, R.H.M. et al., "The Stabilization Of Labile Biochemicals By Undercooling," *Process Biochem.* 22:169–172, Elsevier Science Ltd. (1987).

Hatley, R.H.M. and F. Franks, "Variation in Apparent Enzyme Activity in Two–Enzyme Assay Systems: Phosphoenolpyruvate Carboxylase and Malate Dehydrogenase," *Biotechnol. & Appl. Biochem.* 11:367–370, Portland Press Ltd. (1989).

Heckly, R.J. and J. Quay, "A Brief Review of Lyophilization Damage and Repair in Bacterial Preparations," *Cryobiology* 18:592–597, Academic Press Inc. (1981).

Konev, S.V. et al., "Membrane–structural mechanism of the development of competence in *Escherichia coli* cells to calcium–dependent transfection by bacteriophage λ DNA," *Chem. Abs.* 89:295, Abstract No. 176191q, The American Chemical Society (1978).

Lin, J.–J. and J. Kuo, "AFLP™: A Novel PCR–Based Assay for Plant and Bacterial DNA Fingerprinting," *Focus* 17:66–70, Invitrogen Corporation (1995).

*Merck Index: An Encyclopedia of Chemicals, Drugs, and Biologicals*, 11th edition, Budavari, S. et al., eds., Merck & Co., Inc., Rahway, NJ, p. 3 (1989).

Norrison, D.A., "Transformation and Preservation of Competent Bacterial Cells by Freezing," *Meth. Enzym.* 68:326–331, Academic Press, Ltd. (1979).

Polisky, B. et al., "Specificity of substrate recognition by the EcoRI restriction endonuclease," *Proc. Natl. Acad. Sci. USA* 72:3310–3314, The National Academy of Sciences (1975).

Pope, B. and H.M. Kent, "High efficiency 5 min transformation of *Escherichia coli*," *Nucleic Acids Res.* 24:536–537, Oxford University Press (1996).

Reusch, R.N. et al., "Poly–β–Hydroxybutyrate Membrane Structure and Its Relationship to Genetic Transformability in *Escherichia coli*," *J. Bacteriol.* 168:553–562, American Society for Microbiology (1986).

Simione, Jr., F.P., "Key Issues Relating to the Genetic Stability and Preservation of Cells and Cell Banks,"*J. Parental Sci. & Technol.* 46:336–232. Parental Drug Association, Inc. (1992).

Suzuki, M. and A.A. Szalay, "Bacterial Transformation Using Temperature–Sensitive Mutants Deficient in Peptidoglycan Synthesis," *Meth. Enzym.* 68:331–342, Academic Press (1979).

Tang, X. et al., "The optimization of preparations of competent cells for transformation of *E. coli*," *Nucleic Acids Res.* 22:2857–2858, Oxford University Press (1994).

Trinh, T. et al., "STBL2™: An *Escherichia coli* Strain for the Stable Propagation of Retroviral Clones and Direct Repeat Sequences," *FOCUS* 16:78–80, Invitrogen Corporation (1994).

Ulrich, A.K. et al., "Genetic and Biochemical Analyses of *Escherichia coli* Mutants Altered in the Temperature–Dependent Regulation of Membrane Lipid Composition," *J. Bacteriol.* 154:221–230, American Society for Microbiology (1983).

van Die, I.M. et al., Transformation in *Escherichia coli*: Studies on the Role of the Heat Shock in Induction of Competence, *J. Gen. Microbio.* 129:663–670, Society for General Microbiology (1983).

Wada, H. et al., "Contribution of membrane lipids to the ability of the photosynthetic machinery to tolerate temperature stress," *Proc. Natl. Acad. Sci. USA* 91:4273–4277, The National Academy of Sciences (1994).

Weisburd, S., "Death–Defying Dehydration. Sugars sweeten survival for dried–out animals, membranes and cells," *Science News* 133:107–110, Science Services (1988).

Life Technologies, Inc. 1993–94 Catalogue and Reference Guide, GIBCO BRL, Gaithersburg, MD, pub., pp. 6–10 and 9–4 (1993).

Bullock, W.O. et al., "XL1–Blue: A High Efficiency Plasmid Transforming recA *Escherichia coli* Strain With Beta–Galactosidase Selection," *BioTechniques* 5:376–378, Eaton Publishing Co. (1987).

Cohen, S.N. et al., "Nonchromosomal Antibiotic Resistance in Bacteria: Genetic Transformation of *Escherichia coli* by R–Factor DNA," *Proc. Natl. Acad. Sci. USA* 69:2110–2114, National Academy of Sciences (1972).

Dagert, M. and Ehrlich, S.D., "Prolonged Incubation In Calcium Chloride Improves The Competence Of *Escherichia coli* Cells," *Gene* 6:23–28, Elsevier/North–Holland Biomedical Press (1979).

Dente, L. et al., "pEMBL: a new family of single stranded plasmids," *Nucleic Acids Res.* 11 1645–1655, IRL Press Limited (1983).

Dower, W.J. et al., "High efficiency transformation of *E.coli* by high voltage electroporation," *Nucleic Acids Res.* 16: 6127–6145, IRL Press Limited (1988).

GIBCO–BRL Catalog, Life Technologies, 1993–1994, pp. 9–6 abd 9–10 (1993).

Hamrick, J.L. and R.W. Allard., "Microgeographical Variation in Allozyme Frequencies in *Avena barbata*," *Proc. Natl. Acad. Sci USA* 69:2100–2104, The National Academy of Sciences (1972).

Hanahan, D., "Studies on Transformation of *Escherichia coli* with Plasmids," *J. Mol. Biol.* 166:557–580, Academic Press Inc. (1983).

Hanahan, D. and F.R. Bloom, "Mechanisms of DNA Transformation," in *Escherichia coli* and Salmonella, Neidhardt, F.C. et al., eds., Cellular and Molecular Biology, ASM Press, Washington, DC., pp. 2448–2459, (1996).

Inoune, H. et al., "High efficiency transformation of *Escherichia coli* with plasmids," *Gene* 96:23–28, Elsevier (1990).

Kushner, S.R., "An Improved Method For Transformation of *Escherichia coli* With ColE1 Derived Plasmids," Paper (distributed at meeting) from Proceedings of the International Symposium on Genetic Engineering: Scientific Developments and Practical Applications, Milan, Italy, Mar. 29–31, 1978.

Levinson, A. et al., "Minimal Size Plasmids Containing an M13 Origin for Production of Single–Strand Transducing Particles," *J. Mol. Applied Genet.* 2:507–517, Raven Press (1984).

Liss, L.R., "New M13 Host:DH5αF' Competent Cells," *Focus* 9:13, Invitrogen Coroportion (1987).

Liu, H. and Rashidbaigi, A., "Comparison of Various Competent Cell Preparation Methods for High Efficiency DNA Transformation," *BioTechniques* 8:21–25, Eaton Publishing Co. (1990).

Mandal, M. and Higa, A., "Calcium–dependent Bacteriophage DNA Infection," *J. Mol. Biol.* 53:159–162, Academic Press Ltd. (1970).

Meselson, M. and R. Yuan, "DNA Restriction Enzyme from *E. coli*," *Nature* 217:1110–1114, Nature Publishing Group (1968).

Messing, J., "M13mp2 And Derivitives: A Molecular Cloning System For DNA Sequencing, Strand–Specific Hybridization, And In Vitro Mutagenesis," in *Recombinant DNA. Proceedings of the Third Cleveland Symposium on Macromolecules*, Cleveland, Ohio, Jun. 22–26, 1981, Walton, A.G., ed., Elsevier Scientific Publishing Co., Amsterdam, The Netherlands, pp. 143–153 (1981).

Neumann, E. et al., "Gene transfer into mouse lyoma cells by electroporation in high electric fields," *EMBO J.* 7:841–845, Oxford University Press (1982).

Newman, T. et al., "Cloning and Expression of the ilvB Gene of *Escherichia coli* K–12," *Mol. Gen. Genet.* 186:378–384, Springer–Verlag (1982).

Norgard, M.V. et al., "Factors Affecting The Transformation Of *Escherichia coli* Strain $_x$1776 By pBR322 Plasmid DNA," *Gene* 3:279–292, Elsevier/North–Holland Biomedical Press (1978).

Old, R.W. and Primrose, S.B., "Cloning strategies, gene libraries and cDNA cloning; Recombinant Selection; Expression of cloned DNA molecules," in *Principles of Gene Manipulation*, Carr N.G., ed., Blackwell Scientific Publications, Osney Mead, Oxford, pp. 100–166 (1994).

Old, R.W. and Primrose, S.B., "An Introduction to Genetic Engineering," in *Principles of Gene Manipulation. An Introduction To Genetic Engineering*, Carr, N.G., ed., Blackwell Science, Osney Mead, Oxford, pp. 6–21 (1995).

Potter, H., "Electroporation in Biology: Methods, Applications, and Instrumentation," *Analyt. Biochem.* 174:361–373, Academic Press, Inc. (1988).

Sambrook, J. et al., "Preparation and Transformation of Competent *E. coli*," in *Molecular Cloning*, Sambrook, J., Fritsch, E.F., and Maniatis, T., eds., Cold Spring Harbor Laboratory Press, Cold Spring Harbor, New York, pp. 1.74–1.84 (1989).

Sambrook, J. et al., "Plasmid Vectors," in *Molecular Cloning*, Sambrook, J., Fritsch, E.F., and Maniatis, T., eds. Cold Spring Harbor Laboratory Press, Cold Spring Harbor, New York, p. 1.14 (1989).

Taketo, A., "Sensitivity of *Escherichia coli* to Viral Nucleic Acid, VIII. Idiosyncrasy of $Ca^{2+}$–dependent Competence for DNA," *J. Biochem.* 75:895–904, The Japanese Biochemical Society (1974).

Taketo, A., "Sensitivity of *Escherichia coli* to Viral Nucleic Acid, X, $Ba^{2+}$—Induced Competence for Transfecting DNA," *Z. Naturforsch. Sect. C* 30:520–522, Springer–Verlag (1975).

Taketo, A., "Sensitivity of *Escherichia coli* to Viral Nucleic Acid, XII. $Ca^{2+}$—or $Ba^{2+}$ –Facilitated Transfection of Cell Envelope Mutants," *Z. Naturforsch. Sect. C* 32:429–433, Springer–Verlag (1977).

Tucker, W.T., et al., "Structural and Functional Analysis of the par Region of the pSC101 Plasmid," *Cell* 38:191–201, MIT (1984).

Vieira, J. and Messing, J., "Production of Single–Stranded Plasmid DNA," *Methods Enzymol.* 153:3–11, Academic Press, Inc. (1987).

Yanisch–Perron, C. et al., "Improved M13 phage cloning vectors and host strains: nucleotide sequences of the M13mp18 and pUC19 vectors," *Gene* 33:103–119, Elsevier Science (1985).

Zagursky, R.J. and Berman, M.L., "Cloning vectors that yield high levels of single–stranded DNA for rapid DNA sequencing," *Gene* 27:183–191, Elsevier (1984).

Zimmermann, U. and Vienken, J., "Electric Field–Induced Cell–to–Cell Fusion," *J. Membrane Biol.* 67:165–182, Springer–Verlag (1982).

METHOD CAPABLE OF INCREASING COMPETENCY OF BACTERIAL CELL TRANSFORMATION

CROSS REFERENCE TO RELATED APPLICATIONS

This application is a continuation of U.S. application Ser. No. 08/790,820, filed Jan. 30, 1997, now U.S. Pat. No. 6,274,369, which is based upon and claims priority of U.S. provisional application No. 60/011,040, filed Feb. 2, 1996.

FIELD OF THE INVENTION

The invention relates to improved bacteria, particularly *Escherichia coli* (*E. coli*) bacteria capable of high transformation efficiencies, methods for producing improved bacterial strains capable of high transformation efficiencies, and methods for obtaining high transformation efficiencies with bacteria, particularly *E. coli* bacteria. Specifically, it relates to methods of producing and using bacteria, particularly *E. coli* bacteria that contain F' episome genetic material and are capable of exhibiting enhanced transformation efficiencies.

BACKGROUND OF THE INVENTION

High efficiency chemically competent *E. coli* bacteria (bacterial cells that can be transformed with DNA) are used extensively in the generation of cDNA libraries and the cloning of samples containing small amounts of target sequences. The ability to generate representative cDNA libraries, one in which each mRNA species present in the subject cell is represented in the library, relies on many factors. One of the major factors determining the quality of a cDNA library is the number of clones represented in the library. Using competent bacteria having a high transformation efficiency increases the probability of obtaining rare, under-represented clones in plasmid libraries. Also, when cloning samples containing small amounts of target DNA or cloning the DNA products of complex DNA manipulations such as the DNA products of single or multiple blunt ended ligations, the use of high efficiency bacteria is essential.

Early attempts to achieve transformation of *E. coli* were unsuccessful and it was generally believed that *E. coli* was refractory to transformation. However, Mandel and Higa (*J. Mol. Bio.* 53: 159–162 (1970)) found that treatment with $CaCl_2$ allowed *E. coli* bacteria to take up DNA from bacteriophage λ. In 1972, Cohen et al. showed $CaCl_2$-treated *E. coli* bacteria were effective recipients for plasmid DNA (Cohen et al., *Proc. Natl. Acad. Sci.*, 69: 2110–2114 (1972)). Since transformation of *E. coli* is an essential step or cornerstone in many cloning experiments, it is desirable that it be as efficient as possible (Lui and Rashidbaigi, *BioTechniques* 8: 21–25 (1990)). Several groups of workers have examined the factors affecting the efficiency of transformation.

Hanahan (*J. Mol. Biol.* 166: 557–580 (1983), herein incorporated by reference) examined factors that affect the efficiency of transformation, and devised a set of conditions for optimal efficiency (expressed as transformants per µg of DNA added) applicable to most *E. coli* K12 strains. Typically, efficiencies of $10^7$ to $10^9$ transformants/µg can be achieved depending on the strain of *E. coli* and the method used (Liu & Rashidbaigi, *BioTechniques* 8: 21–25 (1990), herein incorporated by reference).

Many methods for bacterial transformation are based on the observations of Mandel and Higa (*J. Mol. Bio.* 53: 159–162 (1970)). Apparently, Mandel and Higa's treatment induces a transient state of "competence" in the recipient bacteria, during which they are able to take up DNAs derived from a variety of sources. Many variations of this basic technique have since been described, often directed toward optimizing the efficiency of transformation of different bacterial strains by plasmids. Bacteria treated according to the original protocol of Mandel and Higa yield $10^5$–$10^6$ transformed colonies/µg of supercoiled plasmid DNA. This efficiency can be enhanced 100- to 1000-fold by using improved strains of *E. coli* (Kushner, In: *Genetic Engineering: Proceedings of the International Symposium on Genetic Engineering*, Elsevier, Amsterdam, pp. 17–23 (1978); Norgard et al., *Gene* 3:279–292 (1978); Hanahan, *J. Mol. Biol.* 166: 557–580 (1983)) combinations of divalent cations ((Kushner, In: *Genetic Engineering: Proceedings of the International Symposium on Genetic Engineering*, Elsevier, Amsterdam, pp. 17–23 (1978)) for longer periods of time (Dagert and Ehrlich, *Gene* 6: 23–28 (1979)) and treating the bacteria with DMSO (Kushner, In: *Genetic Engineering: Proceedings of the International Symposium on Genetic Engineering*, Elsevier, Amsterdam, pp. 17–23 (1978)), reducing agents, and hexamminecobalt chloride (Hanahan (*J. Mol. Biol.* 166: 557–580 (1983).

Incubation of *E. coli*. in solutions that contain multivalent cations is an important step in the transformation of *E. coli*. A number of multivalent cations are capable of affecting DNA transformation of *E. coli*. In addition to calcium cations, manganese, magnesium and barium cations can affect DNA transformation of *E. coli* and the use of manganese or barium cations rather than calcium cations has lead to higher transformation efficiencies with some strains of *E. coli* (Taketo, Z. *Naturforsch Sect. C* 30: 520–522 (1975); Taketo, Z. *Naturforsch Sect. C* 32: 429–433 (1975); Taketo & Kuno, *J. Biochem.* 75: 895–904 (1975)). A variety of other compounds affect transformation efficiencies. Organic solvents and sulhydryl reagents can also influence transformation efficiencies (Hanahan (*J. Mol. Biol.* 166: 557–580 (1983); Kushner, In: *Genetic Engineering: Proceedings of the International Symposium on Genetic Engineering*, Elsevier, Amsterdam, pp. 17–23 (1978); Jessee, J. A. and Bloom, F. R., U.S. Pat. No. 4,981,797 (1991)).

Incubation of *E. coli* at temperatures around 0° C., often on ice, in buffers containing multivalent cations is an important step in the production or generation of competent cells of *E. coli*. A rapid heat shock or temperature transition after incubation of the *E. coli* with target DNA further improves transformation efficiencies (Mandel and Higra, (*J. Mol. Bio.* 53: 159–162 (1970)). Typically, the solutions containing *E. coli* and target DNA are transferred from 0° C. to temperatures between 37 and 42° C. for 30 to 120 seconds. The temperature at which *E. coli* bacteria are grown prior to incubation at 0° C. can also affect transformation efficiency. Growing *E. coli* bacteria at temperatures between 25 and 30° C. can improve the transformation efficiency of *E. coli* bacteria compared with *E. coli* bacteria grown at 37° C. (Jessee, J. A. and Bloom, F. R., U.S. Pat. No. 4,981,797 (1991)). *E. coli* bacteria that are grown at temperatures between 25 and 30° C., in contrast to 37° C., may require a heat shock at less than 37 to 42° C., or a heat shock of a shorter duration, for optimal results (Jesse and Bloom, U.S. Pat. No. 4,981,797 (1991); Inoue et al. *Gene* 96:23–28 (1990)).

Transformation efficiency can be affected by the *E. coli* strain used. The selection of an *E. coli* strain that is capable of high transformation with the specific competence protocol adopted is an important step in the development of a procedure to produce *E. coli* bacteria capable of high transformation efficiencies. Different strains can exhibit different transformation efficiencies depending on the competence protocol used. Lui and Rashidbaigi, *BioTechniques* 8: 21–25 (1990), compared the transformation efficiency of five *E. coli* strains, HB101, RR1, DH1, SCS1 and JV30 and showed that the transformation efficiencies of these strains varied according to the methodology adopted.

A number of procedures exist for the preparation of competent bacteria and the introduction of DNA into those bacteria. A very simple, moderately efficient transformation procedure for use with *E. coli* involves re-suspending log-phase bacteria in ice-cold 50 mM calcium chloride at about $10^{10}$ bacteria/ml and keeping them ice-cold for about 30 min. Plasmid DNA (0.1 mg) is then added to a small aliquot (0.2 ml) of these now competent bacteria, and the incubation on ice continued for a further 30 min, followed by a heat shock of 2 min at 42° C. The bacteria are then usually transferred to nutrient medium and incubated for some time (30 min to 1 hour) to allow phenotypic properties conferred by the plasmid to be expressed, e.g. antibiotic resistance commonly used as a selectable marker for plasmid-containing cells. Protocols for the production of high efficiency competent bacteria have also been described and many of those protocols are based on the protocols described by Hanahan (*J. Mol. Biol.* 166:557–580 (1983).

The F episome is a genetic element that may exist as a free genetic element or become integrated into the bacterial genome. The presence of the F episome, whether in a free or integrated form, has important consequences for the host bacterium. F-positive bacteria exhibit surface appendages called pilli, which provide attachment sites that facilitate the infection of certain RNA and single-stranded DNA viruses. Many *E. coli* strains have been constructed to contain an F plasmid in order to facilitate the infection of those strains by single-stranded DNA viruses. *E. coli* strains engineered for this purpose include: JM101 (Messing, In *Recombinant DNA: Proceedings of the Third Cleveland Series on Macromolecules*, Elsevier, Amsterdam p 143–153 (1981)); JM105, JM107, JM109 and JM110 (Yanish-Perron et al., *Gene* 33: 103–119 (1985)); TG1 (Gibson, Ph.D. Thesis, Cambridge University, England (1984)); TG2 (Sambrook et al., In *Molecular Cloning: A Laboratory Manual*, Cold Spring Harbor p. 4.14 (1989)); XL1-Blue (Bullock et al., *BioTechniques* 5.4:376–378 (1987)); XS127 and XS101 (Levinson et al., *Mol. Appl. Genet.* 2:507–517 (1984)); 71/18 (Dente et al., *Nucleic Acids Res.* 11: 1645–1655 (1983)); KK2186 (Zagursky and Berman, *Gene* 27:183–191 (1984)); and MV1184 (Viera and Messing, *Methods Enzymol.* 153: 3–11 (1987)).

Transformation efficiency was not thought to be enhanced by the addition of F' episome genetic material. (Hanahan (*J. Mol. Biol.* 166: 557–580 (1983); Bullock et al. (1987)). Indeed, the addition of a F' episome to the *E. coli* strain AG1 produced an *E. coli* strain (XL1-Blue) with a reduced transformation efficiency (Bullock et al. (1987)). Contrary to this background, Applicants' invention involves the use of F' genetic material to provide modified *E. coli* having improved transformation efficiency compared with *E. coli* without F' genetic material.

Another rapid and simple method for introducing genetic material into bacteria is electoporation (Potter, *Anal. Biochem.* 174: 361–73 (1988)). This technique is based upon the original observation by Zimmerman et al., *J. Membr. Biol.* 67: 165–82 (1983), that high-voltage electric pulses can induce cell plasma membranes to fuse. Subsequently, it was found that when subjected to electric shock (typically a brief exposure to a voltage gradient of 4000–16000 V/cm), the bacteria take up exogenous DNA from the suspending solution, apparently through holes momentarily created in the plasma membrane. A proportion of these bacteria become stably transformed and can be selected if a suitable marker gene is carried on the transforming DNA transformed (Newman et al., *Mol. Gen. Genetics* 197: 195–204 (1982)). With *E. coli*, electroporation has been found to give plasmid transformation efficiencies of $10^9$–$10^{10}$/µg DNA (Dower et al., *Nucleic Acids Res.* 16: 6127–6145 (1988)).

Bacterial cells are also susceptible to transformation by liposomes (Old and Primrose, In *Principles of Gene Manipulation: An Introduction to Gene Manipulation*, Blackwell Science (1995)). A simple transformation system has been developed which makes use of liposomes prepared from cationic lipid (Old and Primrose, (1995)). Small unilamellar (single bilayer) vesicles are produced. DNA in solution spontaneously and efficiently complexes with these liposomes (in contrast to previously employed liposome encapsidation procedures involving non-ionic lipids). The positively-charged liposomes not only complex with DNA, but also bind to bacteria and are efficient in transforming them, probably by fusion with the cells. The use of liposomes as a transformation or transfection system is called lipofection.

SUMMARY OF THE INVENTION

The present invention provides novel bacterium, particularly novel *E. coli* bacterium, capable of high efficiency transformation, whose efficiency of transformation is enhanced by the introduction of F' episome genetic material. The invention also concerns methods for the use of novel bacteria, particularly novel *E. coli* bacteria, whose efficiency of transformation is enhanced by the introduction F' episome genetic material. Furthermore, the invention also provides methods for constructing bacteria capable of high efficiency transformation, whose efficiency of transformation is enhanced by the introduction of F' episome genetic material. Indeed, the invention may be used for the insertion of exogenous DNA sequences from other *E. coli* bacteria or other organisms into the novel bacteria of the present invention.

DETAILED DESCRIPTION

One object of the present invention is to provide a bacterium containing F' genetic material capable of an enhanced transformation efficiency. A particular object of the present invention is to provide an *E. coli* bacterium containing F' genetic material capable of an enhanced transformation efficiency.

A further object of the present invention is to provide a process for producing an Enterobacteriacea (especially an *E. coli* bacterium) containing F' genetic material capable of an enhanced transformation efficiency, comprising the following steps: (a) introducing F' genetic material into a bacterium; (b) selecting the bacterium containing F' genetic material; and (c) recovering the bacterium containing F' genetic material.

Another object of the present invention is to provide a process for preparing competent bacteria comprising the following steps: (a) growing a bacterium (especially an *E. coli* bacterium) containing F' genetic material capable of an enhanced transformation efficiency in a growth-conductive medium; and (b) rendering the bacterium competent.

The present invention further concerns a novel bacterium, especially an Enterobacteriacea, and particularly a novel *E. coli* bacterium capable of high efficiency transformation, whose efficiency of transformation is enhanced by the introduction of F' episome genetic material. The present invention also concerns processes for transforming *E. coli* bacterium containing F' genetic material that are capable of enhanced transformation efficiencies.

The present invention pertains to bacteria capable of high efficiency transformation. Such bacteria may be any bacteria whose efficiency of transformation can be enhanced by the introduction of F' episome genetic material. Examples of suitable bacteria include bacteria of the Enterobacteriacea, and in particular, bacteria of the genera Escherichia, Salmonella, especially *E. coli* and Salmonella species. In a preferred embodiment, the bacterium of the present invention may be any *E. coli* strain capable of high efficiency transformation whose efficiency of transformation is enhanced by the introduction of F' episome genetic material. In a further preferred embodiment of the present invention, the bacterium may be any *E. coli* K strain or derivative or equivalent thereof. As used herein, a "derivative" of a bacterium is any bacterium that results from any alteration (or series or alterations), naturally occurring or otherwise, of that bacterium. As used herein, an "equivalent" of a bacterium is any bacterium that has a transformation efficiency (as measured by transformants/μg DNA added) that is equivalent to the transformation efficiency of that bacterium. In an even more preferred embodiment, the bacterium of the present invention will preferably be a derivative of *E. coli* K, such as MM294 (Meselson & Yuan, *Nature* 217: 1110–1114 (1968), or a derivative or equivalent thereof. In a further even more preferred embodiment, the bacterium of the present invention will be preferably be *E. coli* DH5α or a derivative or equivalent thereof, whose efficiency of transformation is enhanced by the introduction of F' episome genetic material. In the most preferred embodiment, the bacterium of the present invention will be more preferably be *E. coli* DH5α, whose efficiency of transformation is enhanced by the introduction of F' episome genetic material.

Transformation, in the context of the current invention, is the process by which exogenous DNA is inserted into a bacterium, causing the bacterium to change its genotype and/or phenotype. Such a change in genotype or phenotype may be transient or otherwise. Exogenous DNA is any DNA, whether naturally occurring or otherwise, from any source that is capable of being inserted into any organism. Preferably, exogenous DNA is any DNA, whether naturally occurring or otherwise, from any source that is capable of being inserted into bacteria. More preferably, exogenous DNA is any DNA, whether naturally occurring or otherwise, from any source that is capable of being inserted into DH5α. Even more preferably, exogenous DNA is any DNA, whether naturally occurring or otherwise, from any source that is capable of being inserted into DH5α bacteria capable of high efficiency transformation, whose efficiency of transformation is enhanced by the introduction of F' episome genetic material. Such exogenous DNA includes, without limitation, plasmid DNA and lambda DNA.

The bacteria of the present invention are capable of acting as a recipient for inserted exogenous DNA. In a preferred embodiment, bacteria capable of acting as a recipient for exogenous DNA are prepared by inoculating medium which supports their growth. In a more preferred embodiment, *E. coli* DH5α bacteria containing F' genetic material capable of an enhanced transformation efficiency are grown at 28° C. in SOB media (20 g bacto-trytone, 5 g bacto-yeast extract, 5 g NaCl, per liter, 2.5 mM KCl, 10 mM $MgCl_2$ equilibrated to pH 7.0 with NaOH) media containing additional multivalent cations until the optical density of the solution was 0.3 $O.D._{550}$ In an even more preferred embodiment, *E. coli* DH5α bacteria containing F' genetic material capable of an enhanced transformation efficiency are grown at 28° C. in SOB media containing 20 mM magnesium cations until the optical density of the solution is 0.3 $O.D._{550}$.

In a preferred embodiment, the bacteria are harvested by centrifugation and resuspended in a solution capable of inducing competence in *E. coli*. In a more preferred embodiment, *E. coli* DH5α bacteria containing F' genetic material capable of an enhanced transformation efficiency are harvested by centrifugation at 4° C. for 10 minuets at 4,000 rpm and resuspended in FSB (10 mM potassium acetate, 100 mM potassium chloride, 45 mM maganese (II) chloride tetrahydrate, 10 mM calcium chloride dihydrate, 3 mM hexammecolbalt (III) chloride, 10% (volume:volume) glycerol, 5% (weight:volume) sucrose, pH 6.4). In an even more preferred embodiment, the re-suspended bacteria containing F' genetic material capable of an enhanced transformation efficiency are subsequently treated with DMSO and can be stored at 70° C. for up to 1 year.

In a preferred embodiment, the bacteria are thawed on ice, mixed with exogenous DNA, incubated on ice, and heat treated. In a more preferred embodiment, the frozen *E. coli* DH5α bacteria containing F' genetic material are thawed on ice for 10 to 15 minuets, mixed with exogenous DNA, incubated on ice for 30 minutes, and heat treated at 42° C. for 45 seconds.

In another embodiment of the present invention, the bacteria are treated with high voltage electric pulses in a solution containing exogenous DNA. In a more preferred alternative embodiment of the present invention, the bacteria are *E. coli* DH5α containing F' genetic material, and are mixed with exogenous DNA and then treated with a brief voltage gradient of 4,000 to 16,000 V/cm.

In a preferred embodiment, high efficiency transformation is preferably $10^8$ or greater transformed bacteria per μg of purified plasmid DNA. High efficiency transformation is more preferably $10^9$ or greater transformed bacteria per μg of purified plasmid DNA.

The present invention also concerns novel *E. coli* bacteria capable of high efficiency transformation, whose efficiency of transformation is enhanced by the introduction of F' episome genetic material. As used herein, such efficiency is said to be "enhanced" if the presence of F' episome genetic material increases the efficiency of transformation of a bacterium. In the preferred embodiment the efficiency of the present invention is enhanced by a factor of greater than one. In a more preferred embodiment, the transformation efficiency of the present invention is enhanced by 2–4 fold. In a even more preferred embodiment, the transformation efficiency of the present invention is enhanced by greater than 4 fold.

The present invention concerns a novel *E. coli* bacterium capable of high efficiency transformation, where said transformation alters the bacterium's genotype and/or transiently alters the bacterium's phenotype. The genotype of an organism is the genetic constitution of an organism. The phenotype of the organism are the characteristics of an organism.

The present invention concerns novel *E. coli* bacteria capable of high efficiency transformation, whose efficiency of transformation is enhanced by the introduction of certain F' episome genetic material. In a preferred embodiment, the bacteria contains all or part of the F' episome genetic material integrated into the *E. coli* chromosome. In another preferred embodiment, the bacteria contains all or part of the F' episome genetic material on a self replicating DNA molecule. In a more preferred embodiment, all or part of the F' episome genetic material is genetically linked to a selectable marker. In an even more preferred embodiment, the F' episome genetic material is linked to an selectable marker providing resistance to an antibiotic, such as a gene providing resistance to tetracycline. In the most preferred embodiment, the F' episome genetic material is derived from the F' episome of XL1-Blue.

The present invention also concerns processes for constructing *E. coli* bacteria containing F' genetic material capable of enhanced transformation efficiencies. In a preferred embodiment, the bacteria of the current invention is obtained by introducing F' genetic material into an *E. coli* bacterium. In a more preferred embodiment of the present invention, the bacterium of the present invention is obtained by mating *E. coli* XL1-Blue and *E. coli* DH5α bacteria. In an even more preferred embodiment of the present invention, the bacteria of the present invention is obtained by mating *E. coli* XL1-Blue and *E. coli* DH5α/pCM301Δ bacteria (Tucker et al. *Cell* 36: 191–201 (1984)).

Having now generally described the invention, the same will be more readily understood through reference to the following examples which are provided by way of illustration, and are not intended to be limiting of the present invention unless specified.

EXAMPLE 1

Construction of the DH5α F'1B Strain

XL1-Blue and XL2-Blue *E. coli* strains can be obtained from Stratagene (11011 N. Torrey Pines Road, La Jolla, Calif. 92037). DH5α *E. coli* strains can be obtained from Life Technologies, Inc., P.O. Box 68, Grand Island, N.Y. 14072-0068. To distinguish between the genotypes of DH5α, XL1-Blue and XL2-Blue *E. coli* strains, DH5α is transformed with a temperature-sensitive plasmid pCM301Δ that exhibits ampicillin resistance. *E. coli* strains DH5α/pCM301Δ, XL1-Blue and XL2-Blue are then streaked out on LB agar plates (LB agar plates: 15 grams per liter bacto-agar in Lennox LB Broth (10 grams tryptone, 5 grams yeast extract, 5 grams NaCl per liter)) containing appropriate antibiotics. The XL1-Blue and XL2-Blue strains are streaked out on LB plates that contained 15 μg/ml tetracycline whereas the DH5α/pCM301Δ bacteria are streaked out on LB plates containing 100 μg/ml ampicillin. The plates are incubated overnight at 30° C.

Individual colonies from each strain are isolated and placed into 1 ml of LB medium and grown at 30° C., without shaking, for 4 hours. After the 4 hours, two matings of the *E. coli* strains are set up by mixing 0.5 ml of the DH5α/pCM301Δ culture with 0.1 ml of the XL1-Blue or XL2-Blue culture and 0.5 ml of fresh Lennox LB Broth medium in a 15 ml culture tube that is incubated for 30 minutes at 30° C. Post-mating, the bacteria are diluted either $10^{-2}$ or $10^{-4}$ with Lennox LB Broth and 100 μl of the resultant solution is applied to LB plates containing 100 μg/ml ampicillin and 15 μg/ml tetracycline. These plates are incubated for between 16 to 18 hours at 30° C. Ten individual colonies are selected from the plates and restreaked for single colony isolation on LB $AMP_{100}$ $TET_{15}$ plates (LB agar plates containing 100 μg/ml ampicillin and 15 μg/ml tetracycline), which are then incubated overnight at 30° C. The colonies are purified through two additional rounds of restreaking on LB $AMP_{100}$ $TET_{15}$ plates grown at 30° C. overnight. The resulting colonies can be designated DH5α F'1 and F'2 corresponding to products from the DH5α/pCM301Δ/XL1-Blue mating and the DH5α/pCM301Δ/XL2-Blue respectively. The temperature sensitive pCM301Δ plasmids are eliminated (cured) from the DH5 α F'1 and DH5α F'2 isolates by growing them at 42° C. in a shaking incubator (250 rpm) for 16 to 18 hours in 1.5 ml of LB containing 15 μg/ml tetracycline. The cured bacteria are purified by streaking for single colonies on LB $TET_{15}$ plates and incubated at 37° C. for 16 to 18 hours. Individual clones are further purified by restreaking on LB $TET_{15}$ plates and incubated for an additional 16 to 18 hours at 37° C. The genotype of the DH5α F'1 and DH5α F'2 isolates are confirmed by attempting to grow the isolates on LB $AMP_{100}$ plates and by growing the isolates on LB X-gal IPTG plates (LB agar plates containing 100 μg/ml X-gal and 40 μg/ml IPTG).

EXAMPLE 2

Production of Competent Bacteria

Working seeds of the DH5α F'1, DH5α F'2, XL1-Blue, XL2-Blue and DH5α strains are generated from single colonies cycled at 28° C. for three days. Cycling single colonies involves isolating a single colony for each restreaked strain and restreaking the isolating colony on the appropriate media. The colonies are then grown for 16–18 hours at 28° C. From these plates a single isolated colony from each strain is selected and then restreaked on the appropriate media and grown for 16–18 hours at 28° C. The process of growing the colonies for 16–18 hours at 28° C. is repeated three times to acclimate the strain to the growth temperature.

Individual colonies are diluted in 1.5 ml of SOB media. 900 μl of the diluted colonies are used to inoculate 50 ml of SOB media with 15 μg/ml tetracycline contained in a 500 ml side baffled flask. The bacteria are then grown at 28° C. in a shaking incubator (250 rpm) until the optical density of the solutions is between 0.5 to 0.7 $OD_{550}$ (about 8 to 10 hours). Seeds are produced by mixing a 10 ml sample from the culture with 10 ml of SOB:glycerol (60:40) in a 50 ml tube. The mixture is then incubated on ice for 10 minutes. Aliquots (0.5 ml) of the seeds are distributed into 1.2 ml Nunc cryotubes and frozen for 5 minutes in a dry ice:ethanol bath. Seeds are stored at −70° C. and used for up to 1 year.

Competent bacteria are produced using a modification of the procedure developed by Hanahan (*J. Mol. Biol.* 166: 557–580 (1983). A seed culture of each strain (DH5α F', XL1-Blue, XL2-Blue and DH5α) are thawed at room temperature and diluted in a ratio of 1:100 with 1 ml SOB containing 20 mM $Mg^{++}$. Aliquots (0.25 ml) of the diluted seed are used to inoculate 2.8 liter baffled Fernbach flasks that contained 1.7 L of SOB/20 mM $Mg^{++}$/100 μg/ml tetracycline. The cultures are incubated at 28° C. in a shaking incubator (275 rpm), until they reach an $OD_{550}$ of 0.5. The bacteria are then harvested by centrifugation in 250 ml Corning centrifuge tubes at 4000 rpm for 10 minutes at 4° C. (2300 g). The supernatant is then drained from the tubes and the bacteria are resuspended in 20 ml FSB +5% sucrose (10 mM potassium acetate, 100 mM potassium chloride, 45 mM maganese (II) chloride tetrahydrate, 10 mM calcium chloride dihydrate, 3 mM hexammecolbalt (III) chloride, 10% (volume:volume) glycerol, 5% (weight:volume) sucrose, pH 6.4). The resuspended bacteria are incubated on ice for 15 minutes. Competence is enhanced by two sequential additions of 0.7 ml DMSO with a 10 minute incubation on ice between additions. After the DMSO additions, the competent bacteria are further incubated on ice for 5 minutes. The competent bacteria are then frozen for 5 minutes in 1.2 ml Nunc Cryotubes containing 0.25 ml of bacteria in a dry ice:ethanol bath. Frozen competent bacteria are stored at −70° C. and are stable for up to 1 year.

EXAMPLE 3

Transformation Procedures

Competent bacteria are removed from −70° C. freezer and thawed on wet ice for about 10 to 15 minutes. Immediately after thawing, the bacteria are gently transferred into prechilled polypropylene tubes and gently agitated. Transformation efficiencies, of the competent bacteria are determined by mixing 5 μl (0.05 ng) of control pUC19 DNA to each tube of competent bacteria and incubating the bacteria on ice for 30 minutes. A heat-shock of the bacteria is carried out at 42° C. for 45 seconds in water bath. Care is taken not to shake the bacteria during the period of the time the bacteria are undergoing heat treatment. The transformation mixtures are then placed on ice for 2 minutes prior to the addition of 0.9 ml of room temperature SOC (SOC medium is identical to SOB medium except that it contains 20 mM glucose) to the transformation mix. The transformation mixtures are incubated at 37° C. for 1 hour in a shaker (225 rpm). The transformation reactions are then diluted in a ratio of 1:100 with SOC medium and 50 μl or 100 μl of the diluted samples are spread on LB plates with 100 μg/ml ampicillin. The plates are then incubated overnight at 37° C.

The total transformants per reaction are determined by adding 25 ng of control pUC19 DNA to each 17×100 mm polypropylene tube of competent bacteria. The DNA are added by moving the pipette through the bacteria and gently taping the bottom of the tube. The bacteria are incubated on ice for 30 minutes and heat-shocked at 42° C. for 45 seconds in water bath. Care is taken not to shake the bacteria during the period of the time the bacteria are undergoing heat treatment. The transformation mix is placed on ice for 2 minutes. After two minutes, 0.9 ml of room temperature SOC is added to the transformation mixture and incubated at 37° C. for 1 hour in a shaker (225 rpm). The transformation reactions are diluted in a ratio of 1:10,000 with SOC medium and then 100 μl of this dilution is spread on LB or YT plates that contained 100 μg/ml ampicillin. The plates are incubated overnight at 37° C.

A viable cell count of the sample is determined by diluting the bacteria in SOC to $10^{-7}$ and then spreading 100 μl from each dilution on LB plates. These plates are incubated overnight at 37° C.

| Sample | Transformation Efficiency (transformants/μg) | Viable Bacteria | Total Transformants |
|---|---|---|---|
| MAX EFFICIENCY | | | |
| DH5α | $1.1 \times 10^9$ | $1.3 \times 10^9$ | $7.7 \times 10^6$ |
| DH5α | $1.4 \times 10^9$ | $1.4 \times 10^9$ | $4.5 \times 10^6$ |
| DH5α F'1 | $6.9 \times 10^9$ | $2.5 \times 10^9$ | $17 \times 10^6$ |
| DH5α F'2 | $6.9 \times 10^9$ | $3.1 \times 10^9$ | $21 \times 10^6$ |
| XL1-Blue | $3.2 \times 10^9$ | $2.4 \times 10^9$ | $11 \times 10^6$ |
| XL2-Blue | $4.3 \times 10^9$ | $2.1 \times 10^9$ | $15 \times 10^6$ |

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

What is claimed is:

1. One or more isolated *E. coli* cells wherein said cells are derived from DH5α and comprise F' genetic material derived from *E. coli* XL1-Blue or *E. coli* XL2-Blue, wherein said *E. coli* cells exhibit a higher transformation efficiency than said *E. coli* cells that do not contain F' genetic material.

2. The *E. coli* cells of claim 1, further comprising exogenous DNA.

3. The *E. coli* cells of claim 2, wherein said exogenous DNA is plasmid DNA.

4. The *E. coli* cells of claim 2, wherein said exogenous DNA is lambda DNA.

5. The *E. coli* cells of claim 1, wherein said cells exhibit a transformation efficiency of $10^8$ or greater transformed bacteria per μg of purified plasmid DNA.

6. The *E. coli* cells of claim 5, wherein said cells exhibit a transformation efficiency of $10^9$ or greater transformed bacteria per μg of purified plasmid DNA.

7. One or more *E. coli* cells obtained by mating *E. coli* DH5α cells with *E. coli* XL1-Blue cells or *E. coli* XL2-Blue cells.

8. The *E. coli* cells of claim 7, wherein said cells are obtained by mating *E. coli* DH5α cells with *E. coli* XL1-Blue cells.

9. The *E. coli* cells of claim 7, wherein said cells are obtained by mating *E. coli* DH5α cells with *E. coli* XL2-Blue cells.

10. A composition comprising:

(a) one or more *E. coli* cells, wherein said cells are derived from DH5α and comprise F' genetic material derived from *E. coli* XL1-Blue or *E. coli* XL2-Blue, wherein said *E. coli* cells exhibit a higher transformation efficiency than said *E. coli* cells that do not contain F' genetic material; and (b) a medium which supports the growth of said *E. coli* cells.

11. The composition of claim 10, further comprising one or more multivalent cations.

12. The composition of claim 11, wherein said one or more multivalent cations are magnesium cations.

13. A composition comprising:

(a) one or more *E. coli* cells wherein said cells are derived from DH5α and comprise F' genetic material derived from *E. coli* XL1-Blue or *E. coli* XL2-Blue, wherein said *E. coli* cells exhibit a higher transformation efficiency than said *E. coli* cells that do not contain F' genetic material; and (b) a solution capable of inducing competence in *E. coli*.

14. The composition of claim 13, wherein said solution capable of inducing competence in *E. coli* comprises one or more ingredients selected from the group consisting of: potassium acetate, potassium chloride, manganese (II) chloride tetrahydrate, calcium chloride dihydrate, hexaminecobalt (III) chloride, glycerol and sucrose.

15. The composition of claim 14, wherein said solution capable of inducing competence in *E. coli* comprises 10 mM potassium acetate, 100 mM potassium chloride, 45 mM manganese (II) chloride tetrahydrate, 10 mM calcium chloride dihydrate, 3 mM hexaminecobalt (III) chloride, 10% glycerol and 5% sucrose.

16. The composition of claim 13, further comprising dimethylsulfoxide (DMSO).

17. The composition of claim 13, further comprising exogenous plasmid DNA.

* * * * *